United States Patent
Iwakiri et al.

(10) Patent No.: US 9,753,159 B2
(45) Date of Patent: Sep. 5, 2017

(54) RADIOGRAPHIC IMAGING CONTROL DEVICE, RADIOGRAPHIC IMAGING SYSTEM, RADIOGRAPHIC IMAGING DEVICE CONTROL METHOD, AND RECORDING MEDIUM

(71) Applicant: FUJIFILM Corporation, Tokyo (JP)

(72) Inventors: Naoto Iwakiri, Kanagawa (JP); Kouichi Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 459 days.

(21) Appl. No.: 14/264,285

(22) Filed: Apr. 29, 2014

(65) Prior Publication Data

US 2014/0233701 A1 Aug. 21, 2014

Related U.S. Application Data

(63) Continuation of application No. PCT/JP2012/080093, filed on Nov. 20, 2012.

(30) Foreign Application Priority Data

Feb. 22, 2012 (JP) .................................. 2012-036717

(51) Int. Cl.
*G01T 1/24* (2006.01)
*G01T 1/20* (2006.01)
(Continued)

(52) U.S. Cl.
CPC ................ *G01T 1/247* (2013.01); *A61B 6/42* (2013.01); *A61B 6/5258* (2013.01); *G01T 1/17* (2013.01);
(Continued)

(58) Field of Classification Search
CPC ........... A61B 6/00; A61B 6/42; A61B 6/4208; A61B 6/4233; A61B 6/4266; A61B 6/52;
(Continued)

(56) References Cited

U.S. PATENT DOCUMENTS

2008/0011958 A1* 1/2008 Endo .................... A61B 6/4488
250/370.08
2009/0218501 A1 9/2009 Kondou
(Continued)

FOREIGN PATENT DOCUMENTS

| JP | 2005-176098 A | 6/2005 |
| JP | 2009-207570 A | 9/2009 |
| WO | WO 2010/044153 A1 | 4/2010 |

OTHER PUBLICATIONS

Foreign Office Action of JP2014-500871 dated Feb. 17, 2015.
(Continued)

*Primary Examiner* — Anastasia Midkiff
(74) *Attorney, Agent, or Firm* — Birch, Stewart, Kolasch & Birch, LLP

(57) ABSTRACT

A radiographic imaging control device is provided with a radiation detector, amplifiers and a controller. A plurality of pixels are arrayed in the radiation detector, each pixel including a sensor portion that generates charges in accordance with irradiated radiation and a switching element that is for reading out the charges generated at the sensor portion. Each amplifier is provided in correspondence with a respective pixel of the radiation detector, is equipped with a resetter that resets charges remaining at an integration capacitor, and amplifies an electronic signal according to the charges read out by the switching element from the corresponding pixel by a pre-specified amplification factor. In accordance with pre-specified conditions, the controller controls so as to alter a bias current supplied to the amplifiers in at least some periods of resetting by the resetter.

18 Claims, 12 Drawing Sheets

(51) Int. Cl.

| | | |
|---|---|---|
| *H04N 5/32* | (2006.01) | |
| *H01L 27/146* | (2006.01) | |
| *H01L 27/148* | (2006.01) | |
| *H03K 21/38* | (2006.01) | |
| *A61B 6/00* | (2006.01) | |
| *G01T 1/208* | (2006.01) | |
| *H04N 5/374* | (2011.01) | |
| *G01T 1/17* | (2006.01) | |
| *H04N 5/378* | (2011.01) | |
| *H04N 5/3745* | (2011.01) | |
| *H04N 5/343* | (2011.01) | |

(52) U.S. Cl.
CPC ........ *G01T 1/208* (2013.01); *H01L 27/14601* (2013.01); *H01L 27/14609* (2013.01); *H01L 27/14676* (2013.01); *H01L 27/14806* (2013.01); *H03K 21/38* (2013.01); *H04N 5/3741* (2013.01); *A61B 6/4233* (2013.01); *A61B 6/4283* (2013.01); *A61B 6/54* (2013.01); *H01L 27/146* (2013.01); *H01L 27/14658* (2013.01); *H04N 5/32* (2013.01); *H04N 5/343* (2013.01); *H04N 5/378* (2013.01); *H04N 5/37457* (2013.01)

(58) Field of Classification Search
CPC ....... A61B 6/5205; A61B 6/5258; A61B 6/54; A61B 2560/00; A61B 2560/02; A61B 2562/00; A61B 2562/04; A61B 2562/043; A61B 2562/046; A61B 2576/00; G01T 1/00; G01T 1/16; G01T 1/161; G01T 1/17; G01T 1/20; G01T 1/2006; G01T 1/2018; G01T 1/208; G01T 1/24; G01T 1/243; G01T 1/246–1/248; G01T 7/00; H03K 21/00; H03K 21/08; H03K 21/38; H03K 2217/00; H03K 2217/94; H04N 5/30; H04N 5/32; H04N 5/321; H04N 5/335; H04N 5/3355; H04N 5/341; H04N 5/343; H04N 5/351; H04N 5/369; H04N 5/3698; H04N 5/374; H04N 5/3741; H04N 5/3742; H04N 5/3745; H04N 5/37455; H04N 5/37457; H04N 5/378; H04N 2201/0079; H01L 25/00; H01L 25/03; H01L 25/04; H01L 25/065; H01L 25/0655; H01L 25/16; H01L 25/167; H01L 25/18; H01L 31/00; H01L 31/08; H01L 31/085; H01L 31/10; H01L 31/115; H01L 27/00; H01L 27/14; H01L 27/144; H01L 27/1446; H01L 27/146; H01L 27/14601; H01L 27/14609; H01L 27/14643; H01L 27/14658; H01L 27/14663; H01L 27/14659; H01L 27/14661; H01L 27/14665; H01L 27/14676; H01L 27/148; H01L 27/14806; H01L 27/14825; H01L 27/14831; H01L 27/14893
See application file for complete search history.

(56) References Cited

U.S. PATENT DOCUMENTS

| | | | |
|---|---|---|---|
| 2011/0199523 A1 | 8/2011 | Tanabe et al. | |
| 2012/0132824 A1* | 5/2012 | Nishino | H04N 5/32 |
| | | | 250/394 |
| 2013/0001426 A1* | 1/2013 | Tredwell | G01T 1/2018 |
| | | | 250/370.09 |

OTHER PUBLICATIONS

International Search Report issued in PCT/JP2012/080093, mailed on Dec. 18, 2012.
Written Opinion issued in PCT/JP2012/080093, mailed on Dec. 18, 2012.
Foreign Office Action of JP2014-500871 dated Sep. 15, 2015.
Chinese Office Action and Search Report, dated Sep. 5, 2016, for Chinese Application No. 201280060354.4, with an English Translation of the Chinese Office Action.

* cited by examiner

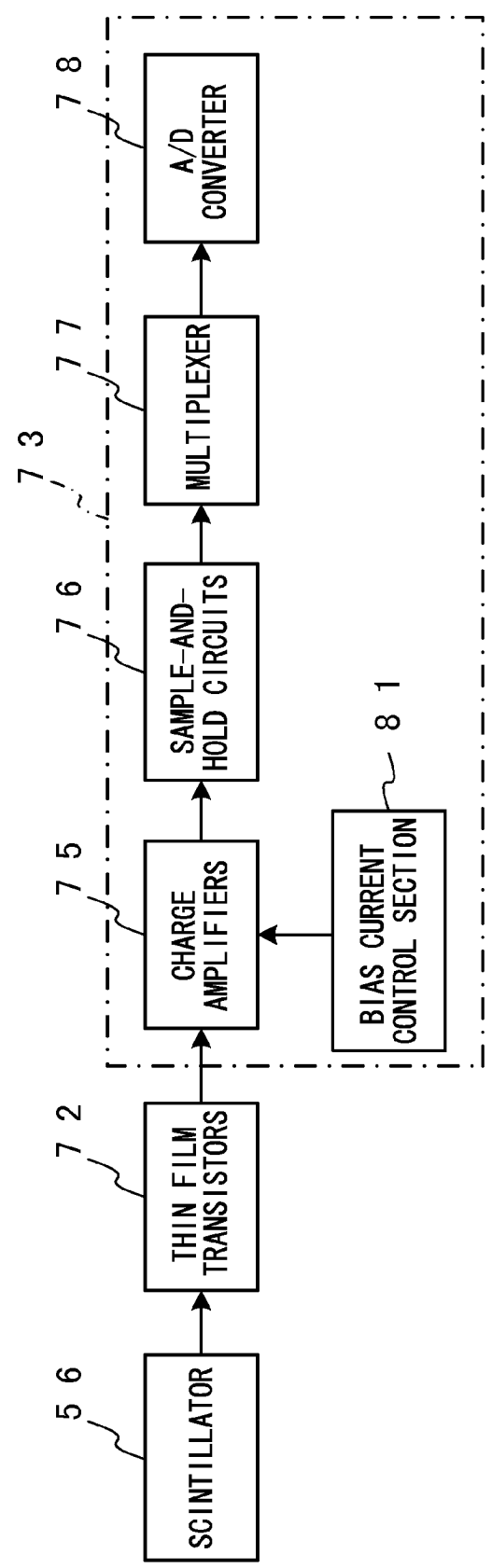

RADIOGRAPHIC IMAGING CONTROL DEVICE, RADIOGRAPHIC IMAGING SYSTEM, RADIOGRAPHIC IMAGING DEVICE CONTROL METHOD, AND RECORDING MEDIUM

CROSS-REFERENCE TO RELATED APPLICATION

This application is a continuation application of International Application No. PCT/JP/2012/080093, filed Nov. 20, 2012, the disclosure of which is incorporated herein by reference in its entirety. Further, this application claims priority from Japanese Patent Application No. 2012-036717, filed Feb. 22, 2012, the disclosure of which is incorporated herein by reference in its entirety.

BACKGROUND OF THE INVENTION

Field of the Invention

The present invention relates to a radiographic imaging control device, a radiographic imaging system, a radiographic imaging device control method, and a recording medium.

Description of the Related Art

In recent years, radiation detectors (sometimes referred to as electronic cassettes and the like) such as flat panel detectors (FPD) and the like have been realized. In an FPD, a radiation-sensitive layer is disposed on a thin film transistor (TFT) active matrix substrate, and the FPD is capable of converting radiation amounts to digital data (electronic signals). A radiographic imaging device that uses this radiation detector to capture radiation images expressed by amounts of irradiated radiation has been realized.

In this radiation detector, charges corresponding to radiation amounts are accumulated and read out, and signal processing is applied thereto. As an example of a device that carries out the signal processing, the technology recited in, for example, Japanese Patent Application Laid-Open (JP-A) No. 2009-207570 has been proposed.

The technology recited in JP-A No. 2009-207570 has a configuration in which signal charges outputted from individual pixel portions of a radiation detection panel are integrated by integration circuit sections and amplified by amplification sections, converted from parallel to serial data by sample-and-hold sections and a multiplexer, then amplified by an amplifier and converted to digital data by an analog-to-digital conversion section. A bias current supply section that supplies bias currents to the integration circuit sections, the amplification sections, the sample-and-hold sections, the multiplexer and the amplifier is connected thereto. When an operation mode is a high-speed mode, a bias current control section increases the bias currents supplied to circuits subsequent to and including the multiplexer but reduces the bias currents supplied to circuits prior to and including the sample-and-hold sections. When the operation mode is a low-noise mode, the bias current control section increases the bias currents supplied to the circuits prior to and including the sample-and-hold sections but reduces the bias currents supplied to the circuits subsequent to and including the multiplexer. Thus, fast-output operations and low-noise operations are possible with heat generation amounts being suppressed.

SUMMARY

When a high-speed mode (a fast frame rate) is to be implemented, a reset duration between samples is a significant factor. The technology of JP-A No. 2009-207570 gives no consideration at all to shortening a reset duration of the integration circuit sections.

The present invention has been made in consideration of the situation described above, and an object of the invention is to reduce an imaging duration.

In order to solve the problem described above, a radiographic imaging control device according to the present invention includes: a radiation detector in which a plurality of pixels are arrayed, each pixel including a sensor portion that generates charges in accordance with irradiated radiation and a switching element that is for reading out the charges generated at the sensor portion; an amplifier that is provided in correspondence with a respective pixel of the radiation detector, is equipped with a resetter that resets charges remaining at an integration capacitor, and amplifies an electronic signal according to the charges read out by the switching element from the corresponding pixel by a pre-specified amplification factor; and a controller that, in accordance with a pre-specified condition, controls so as to alter a bias current supplied to the amplifier in at least some periods of resetting by the resetter.

BRIEF DESCRIPTION OF DRAWINGS

FIG. 4 is a block diagram showing schematic structure of a signal processing section of the radiation detector in accordance with the exemplary embodiment;

DETAILED DESCRIPTION

Figure 1:
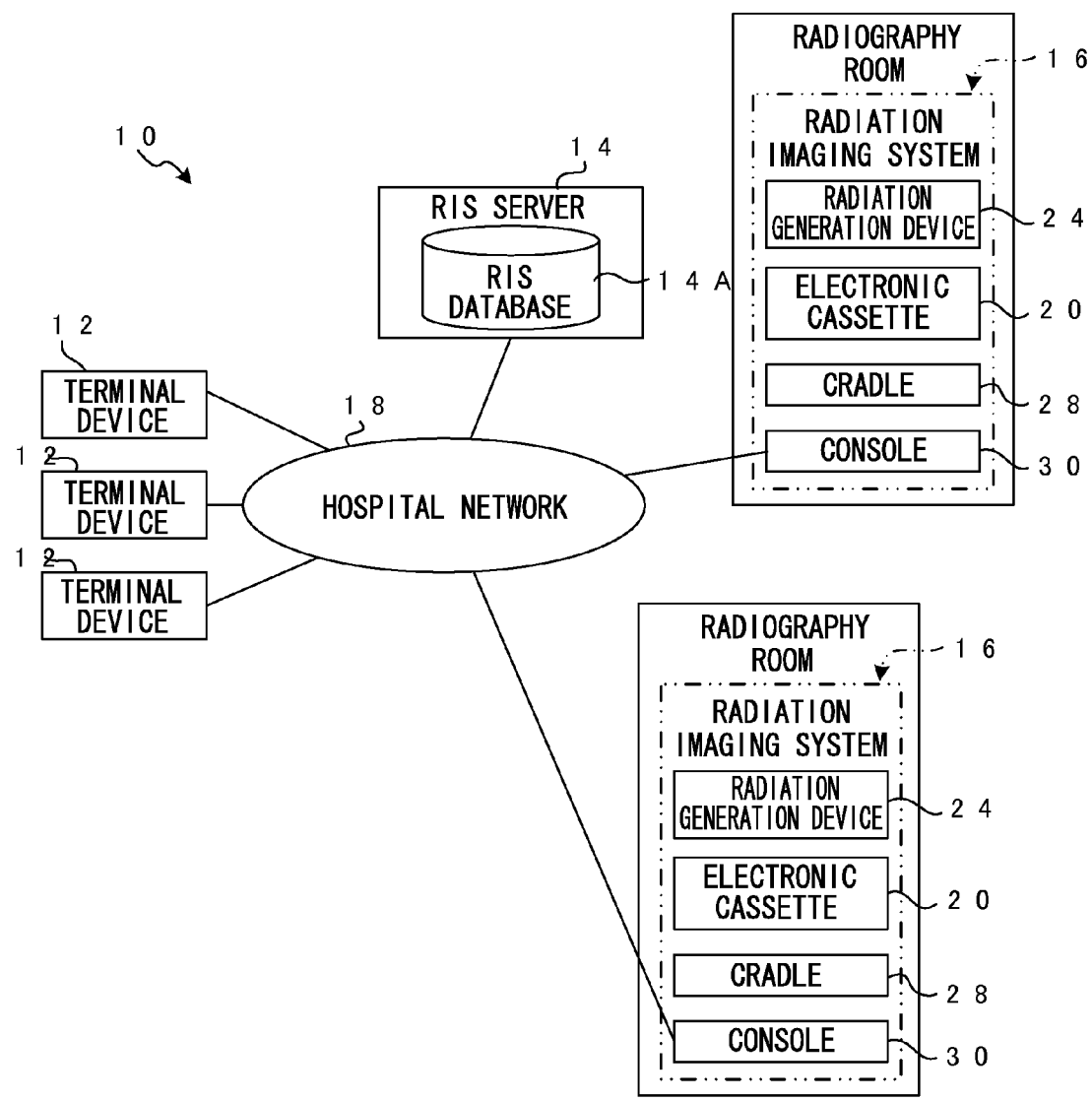
FIG. 1 is a block diagram illustrating the structure of a radiology information system in accordance with an exemplary embodiment.

FIG. 1 is a schematic structural diagram of a radiology information system (hereinafter referred to as an RIS) 10 according to an exemplary embodiment of the present invention. The RIS 10 may capture both still images and video images. The definition of the term "video images" as used herein includes successive still images being rapidly displayed so as to be interpreted as moving images, in which a process of capturing a still image, converting it to electronic signals, transferring the electronic signals, and replaying the still image from the electronic signals is rapidly repeated. Thus, depending on the degree of "rapidity", imaging of (a portion or the whole of) the same region a plural number of times in a pre-specified duration and successively replaying the images, which is known as "frame advance", is also encompassed by the term "video images".

The RIS 10 is a system for administering information of clinical appointments, medical records and so forth in the radiology department, and constitutes a portion of a hospital information system (hereinafter referred to as an HIS).

The RIS 10 is constituted with a plural number of imaging request terminal devices (hereinafter referred to as terminal devices) 12, an RIS server 14 and a radiographic imaging system (hereinafter referred to as an imaging system) 16, which is separately installed in a radiography imaging room (or an operating room) in the hospital, being connected to a hospital internal network 18, which is formed with a wired and/or wireless local area network (LAN) or the like. An HIS server that administers the HIS as a whole is also connected to the hospital internal network 18. One or three or more of the imaging system 16 may be installed; in FIG. 1, an imaging system 16 is installed in each imaging room but two or more of the imaging system 16 may be installed in one imaging room.

Each terminal device 12 is for a doctor, a radiographer or the like to input and monitor clinical information, facility reservations and the like, and imaging requests and imaging bookings for radiation images are made via the terminal device 12. The terminal device 12 includes a personal computer with a display device, and is connected with the RIS server 14 via the hospital internal network 18, enabling communications therebetween.

The RIS server 14 receives imaging requests from the terminal devices 12 and manages an imaging schedule for radiographic images at the imaging system 16. The RIS server 14 is configured to include a database 14A.

The database 14A is constituted to include: information relating to patients, such as information on attributes (name, gender, date of birth, age, blood type, body weight, a patient identification (ID) number and so forth) of each patient (imaging subject), medical record, treatment history, previously imaged radiation images, and the like; information relating to electronic cassettes 20 used in the imaging system 16 which are described below, such as an identification number (ID information) of each electronic cassette 20 and the type, size, sensitivity, the date of first use, the number of uses, and the like; and environmental information representing environments in which the electronic cassettes 20 are used to capture radiation images, which is to say environments in which the electronic cassettes 20 are employed (for example, a radiography imaging room, an operating room and the like).

Data relating to medical treatments administered by a medical institution may be stored substantially permanently and, when required, personal information on the history of patients (imaging subjects) and the like may be retrieved from a server outside the hospital using a system for temporarily retrieving data from required locations (which may be referred to as a "medical cloud" or the like).

The imaging system 16 carries out imaging of radiation images in response to instructions from the RIS server 14, in accordance with control by doctors, radiographers and the like. The imaging system 16 is also equipped with a radiation generation device 24, the electronic cassette 20, which incorporates a radiation detector 26 (see FIG. 3A), a cradle 28, which charges a battery incorporated in the electronic cassette 20, and a console 30, which controls the electronic cassette 20 and the radiation generation device 24. Under the control of a radiation irradiation control unit 22 (see FIG. 4), the radiation generation device 24 irradiates radiation X from a radiation irradiation source 22A that irradiates the radiation X in radiation amounts depending on irradiation conditions. The radiation detector 26 absorbs radiation X that has passed through an imaging target location of the patient, generates electric charges and, on the basis of the generated charge amounts, generates image information representing a radiation image.

The console 30 acquires various kinds of information contained in the database 14A from the RIS server 14, stores the information in a hard disc drive (HDD) 88 (see FIG. 6), which is described below, and uses this information to control the electronic cassette 20 and the radiation generation device 24 in accordance with needs.

Figure 2:
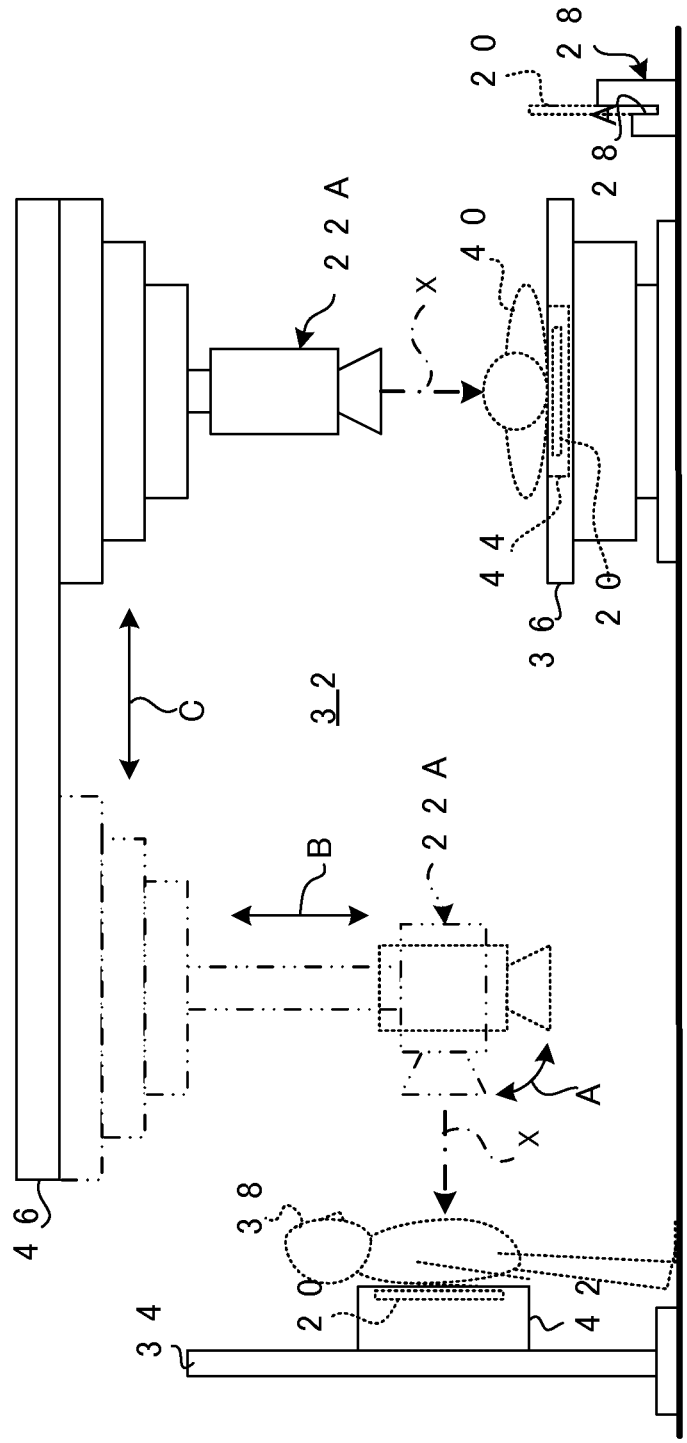
FIG. 2 is a side view showing an example of a state of arrangement of devices in a radiography imaging room of a radiation image capture system in accordance with the exemplary embodiment.

FIG. 2 shows an example of a state of arrangement of devices in a radiography imaging room 32 of the imaging system 16 in accordance with the present exemplary embodiment.

As shown in FIG. 2, in the radiography imaging room 32, a standing table 34 that is used when radiographic imaging is being carried out on an imaging subject in a standing position and a reclining table 36 that is used when radiographic imaging is being carried out on an imaging subject in a reclining position are provided. A space forward of the standing table 34 serves as an imaging position of an imaging subject 38 when radiographic imaging is being carried out in the standing position, and a space above the reclining table 36 serves as an imaging position of an imaging subject 40 when radiographic imaging is being carried out in the reclining position.

A retention portion 42 that retains the electronic cassette 20 is provided at the standing table 34. When a radiation image is being imaged in the standing position, the electronic cassette 20 is retained by the retention portion 42. Similarly, a retention portion 44 that retains the electronic cassette 20 is provided at the reclining table 36. When a radiation image is being imaged in the reclining position, the electronic cassette 20 is retained by the retention portion 44.

In the radiography imaging room 32, in order that both radiographic imaging in the standing position and radiographic imaging in the reclining position are possible with radiation from the single radiation irradiation source 22A, a support and movement mechanism 46 is provided that supports the radiation irradiation source 22A to be turnable about a horizontal axis (in the direction of arrow A in FIG. 2), movable in a vertical direction (the direction of arrow B in FIG. 2) and movable in a horizontal direction (the direction of arrow C in FIG. 2). A drive source is incorporated in the support and movement mechanism 46 and moves the radiation irradiation source 22A in the directions of arrows A, B and C in FIG. 2 (including rotation).

In the cradle 28, an accommodation portion 28A capable of accommodating the electronic cassette 20 is formed.

When the electronic cassette 20 is accommodated in the accommodation portion 28A of the cradle 28, the battery incorporated in the electronic cassette 20 is charged up. When a radiation image is to be imaged, the electronic cassette 20 is taken from the cradle 28 by a radiographer or the like. If a posture for imaging is to be the standing position, the electronic cassette 20 is retained at the retention portion 42 of the standing table 34, and if the posture for imaging is to be the reclining position, the electronic cassette 20 is retained at the retention portion 44 of the reclining table 36.

In the imaging system 16 according to the present exemplary embodiment, various kinds of information (described in more detail below) are exchanged by wireless communication between the radiation generation device 24 and the console 30 and between the electronic cassette 20 and the console 30.

The electronic cassette 20 is not used only in conditions in which it is retained by the retention portion 42 of the standing table 34 or the retention portion 44 of the reclining table 36. The electronic cassette 20 is portable, and therefore may be used in conditions in which it is not retained at a retention portion, for imaging arm areas, leg areas and the like.

A radiation detector, which is described below, is incorporated in the electronic cassette 20. The radiation detector may use either of an indirect conversion system that converts radiation to light using a scintillator and then converts the light to electronic charges with photoelectric conversion elements such as photodiodes or the like, or a direct conversion system that converts radiation to electronic charges in a semiconductor layer of amorphous selenium or the like. A direct conversion system radiation detector is structured by a photoelectric conversion layer that absorbs the radiation X and converts the same to electric charges being layered on a TFT active matrix substrate. The photoelectric conversion layer is formed of, for example, non-crystalline amorphous selenium (a-Se) in which selenium is a principal constituent (for example, a content of at least 50%). When the radiation X is irradiated on the photoelectric conversion layer, charges (electron-hole pairs) are generated within the photoelectric conversion layer in accordance with irradiated radiation amounts. Thus, the irradiated radiation X is converted to charges. An indirect conversion system radiation detector converts the radiation X to charges indirectly using a fluorescent material and photoelectric conversion elements (photodiodes) in place of a radiation-charge conversion material such as amorphous selenium that converts the radiation X to charges directly. Terbium-activated gadolinium oxysulfide ($Gd_2O_2S$:Tb, shortened to "GOS") and Thallium-activated cesium iodide (CsI:Tl) are well known as fluorescent materials. In this case, the radiation X is converted to light by the fluorescent material and the light is converted to charges by the photodiodes that are photoelectric conversion elements. The electronic cassette 20 according to the present exemplary embodiment is described herein as incorporating an indirect conversion system radiation detector.

Figure 3A:
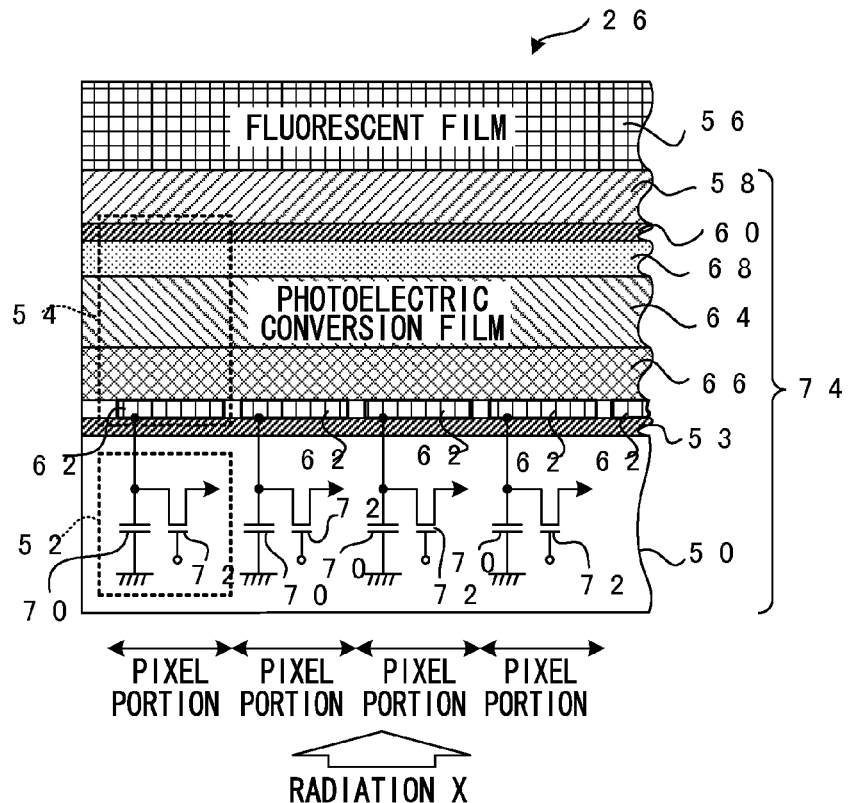
FIG. 3A is a sectional schematic diagram showing schematic structure of a four-pixel portion of a radiation detector in accordance with the exemplary embodiment.
Figure 3B:
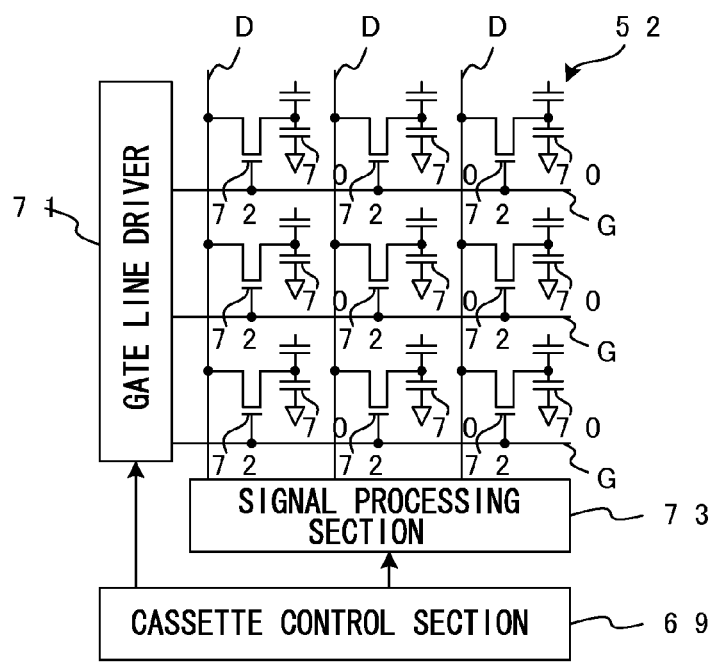
FIG. 3B is a diagram showing the electronic configuration of a pixel portion of the radiation detector in accordance with the exemplary embodiment.

FIG. 3A is a sectional schematic diagram schematically showing the structure of a four-pixel portion of the radiation detector 26 installed in the electronic cassette 20. FIG. 3B is a diagram showing the electronic configuration of a pixel portion of the radiation detector 26.

As shown in FIG. 3A, in the radiation detector 26, signal output portions 52, sensor portions 54 (a TFT substrate 74) and a scintillator 56 are sequentially layered on an insulating substrate 50, and pixel groups of the TFT substrate 74 are constituted by the signal output portions 52 and sensor portions 54. That is, a plural number of pixels are arrayed in a matrix pattern on the substrate 50 and, at each pixel, the signal output portion 52 and the sensor portion 54 are superposed. An insulating film 53 is provided between the signal output portions 52 and the sensor portions 54.

The scintillator 56 is formed over the sensor portions 54 with a transparent insulating film 58 therebetween. The scintillator 56 is a film formed of a fluorescent material that converts radiation that is incident from above (the opposite side thereof from the side at which the substrate 50 is disposed) or below to light and emits the light. Because of the provision of the scintillator 56, radiation that has passed through an imaging subject is absorbed and light is emitted.

The wavelength range of the light emitted by the scintillator 56 is preferably in the visible light range (wavelengths from 360 nm to 830 nm). To enable monochrome imaging by the radiation detector 26, it is more preferable if a green wavelength range is included.

Specifically, if X-rays are used as the radiation and imaged, it is preferable if the fluorescent material used in the scintillator 56 includes cesium iodide (CsI). It is particularly preferable to use cesium iodide with thallium added thereto (CsI(Tl)), which has a light emission spectrum with a wavelength range of 420 nm to 700 nm when X-rays are irradiated thereon. CsI(Tl) has a light emission peak wavelength of 565 nm, in the visible light region.

In the present exemplary embodiment, an example is illustrated in which an irradiation side sampling (ISS) system is employed, in which the TFT substrate 74 is disposed at the side of the scintillator 56 of the face on which the radiation is irradiated. However, a penetration side sampling (PSS) system may be employed in which the TFT substrate is disposed at the opposite side of the scintillator from the side at which the radiation is incident. A scintillator emits light more strongly at the side thereof on which radiation is incident. Therefore, in irradiation side sampling (ISS) in which the TFT substrate is disposed at the radiation incidence side of the scintillator, light emission positions of the scintillator are closer to the TFT substrate than in penetration side sampling (PSS) in which the TFT substrate is disposed at the opposite side of the scintillator from the radiation incidence side thereof. Therefore, with ISS the resolution of radiation images obtained by imaging is higher and, because light amounts received at the TFT substrate are larger, the radiographic imaging sensitivity is improved.

Each sensor portion 54 includes an upper electrode 60, a lower electrode 62, and a photoelectric conversion film 64 disposed between the upper and lower electrodes. The photoelectric conversion film 64 is constituted with an organic photoelectric conversion material that absorbs the light emitted by the scintillator 56 and generates charges.

Because the light produced by the scintillator 56 must be incident on the photoelectric conversion film 64, the upper electrode 60 is preferably constituted with a conductive material that is transparent at least to a wavelength of light emitted from the scintillator 56. Specifically, it is preferable to use transparent conducting oxides (TCO) which have high transparency to visible light and low resistance values. A thin metal film of gold or the like may be used as the upper electrode 60. However, if the transparency is to be 90% or above, the resistance value is likely to be high. Therefore, a TCO is more preferable. For example, ITO, IZO, AZO, FTO, $SnO_2$, $TiO_2$, $ZnO_2$ or the like may be preferably used. In regard to ease of processing, low resistance and transparency, ITO is the most preferable. Herein, the upper electrode 60 may be structured as a single common electrode for all pixels, or may be divided between the individual pixels.

The photoelectric conversion film 64 includes an organic photoelectric conversion material, absorbs light emitted from the scintillator 56, and generates electric charges in accordance with the absorbed light. If the photoelectric conversion film 64 includes this organic photoelectric conversion material, the film has a sharp absorption spectrum in the visible range and hardly any electromagnetic waves apart from the light emitted by the scintillator 56 are absorbed by the photoelectric conversion film 64. Thus, noise that is produced when radiation such as X-rays and the like is absorbed by the photoelectric conversion film 64 may be effectively suppressed.

For the organic photoelectric conversion material of the photoelectric conversion film 64 to absorb the light emitted by the scintillator 56 most efficiently, it is preferable that the absorption peak wavelength of the organic photoelectric conversion material be as close as possible to the light emission peak wavelength of the scintillator 56. It is ideal if the absorption peak wavelength of the organic photoelectric conversion material and the light emission peak wavelength of the scintillator 56 match. However, provided a difference between the two is small, the light emitted from the scintillator 56 can be satisfactorily absorbed. In specific terms, it is preferable if the difference between the absorption peak wavelength of the organic photoelectric conversion material and the light emission peak wavelength of the scintillator 56 in response to the radiation is not more than 10 nm, and it is more preferable if the difference is not more than 5 nm.

Organic photoelectric conversion materials that may satisfy these conditions include, for example, quinacridone-based organic compounds and phthalocyanine-based organic compounds. For example, an absorption peak wavelength of quinacridone in the visible region is 560 nm. Therefore, if quinacridone is used as the organic photoelectric conversion material and CsI(Tl) is used as the material of the scintillator 56, the difference between the peak wavelengths may be kept to within 5 nm, and charge amounts generated in the photoelectric conversion film 64 may be substantially maximized. The photoelectric conversion film 64 that contains an organic photoelectric conversion material is described as an example in the present exemplary embodiment, but this is not a limitation. It is sufficient that the photoelectric conversion film 64 has a material that absorbs light and generates charges, and other materials such as, for example, amorphous silicon may be employed. In a case in which the photoelectric conversion film 64 is constituted with amorphous silicon, the photoelectric conversion film 64 may be constituted so as to absorb light emitted from the scintillator over a broad wavelength range.

It is sufficient that the sensor portion 54 structuring each pixel includes at least the lower electrode 62, the photoelectric conversion film 64 and the upper electrode 60. However, to suppress an increase in dark current, it is preferable to provide one or other of an electron blocking film 66 and a hole blocking film 68, and it is more preferable to provide both.

The electron blocking film 66 may be provided between the lower electrode 62 and the photoelectric conversion film 64. When a bias voltage is applied between the lower electrode 62 and the upper electrode 60, electrons are injected from the lower electrode 62 to the photoelectric conversion film 64. Thus, an increase in the dark current may be suppressed. An organic material with electron affinity may be used for the electron blocking film 66.

The hole blocking film 68 may be provided between the photoelectric conversion film 64 and the upper electrode 60. When the bias voltage is applied between the lower electrode 62 and the upper electrode 60, holes are injected from the upper electrode 60 to the photoelectric conversion film 64. Thus, an increase in the dark current may be suppressed. An organic material with electron acceptance may be used for the hole blocking film 68.

Each signal output portion 52 is formed with a capacitor 70, which corresponds with the lower electrode 62 and accumulates charges that have migrated to the lower electrode 62, and a field effect-type thin film transistor (which may hereinafter be referred to simply as a thin film transistor) 72, which converts the charges accumulated at the capacitor 70 to electronic signals and outputs the electronic signals. A region in which the capacitor 70 and the thin film transistor 72 are formed includes a region that overlaps with the lower electrode 62 in plan view. Because of this structure, the signal output portion 52 and the sensor portion 54 are superposed in the thickness direction. To minimize a planar area of the radiation detector 26 (the pixels), it is desirable if the region in which each capacitor 70 and thin film transistor 72 are formed is completely covered by the lower electrode 62.

As shown in FIG. 3B, the signal output portions 52 of the pixels arranged in the matrix pattern are provided with a plural number of gate lines G and a plural number of data lines D. The gate lines G extend in a certain direction (a row direction) and are for turning the thin film transistors 72 of the individual pixels on and off. The data lines D extend in a direction crossing the gate lines G and are for reading accumulated charges from the capacitors 70 via the thin film transistors 72 that have been turned on. The individual gate lines G are connected to a gate line driver 71, and the individual data lines D are connected to a signal processing section 73. When charges are accumulated at the capacitors 70 of the individual pixel portions, the thin film transistors 72 of the individual pixel portions are sequentially turned on one row at a time by signals supplied through the gate lines G from the gate line driver 71. The charges accumulated in the capacitors 70 of the pixel portions for which the thin film transistors 72 have been turned on are propagated through the data lines D as analog charge signals and inputted to the signal processing section 73. Thus, the charges accumulated at the capacitors 70 of the individual pixel portions are sequentially read out in row units.

The gate line driver 71 is capable of both a sequential scanning system (a progressive scanning system) and a binning readout system. In an operation for reading out a single image with the sequential scanning system, the gate line driver 71 outputs on-signals to the gate lines G one line at a time and reads out charges accumulated at the capacitors 70 of the pixel portions one line at a time. In an operation for reading out a single image with the binning readout system, the gate line driver 71 sequentially outputs on-signals to the gate lines G in sets of a plural number of lines (for example, two lines or four lines) and reads the charges accumulated at the capacitors 70 of the pixel portions in the plural number of lines (simultaneously reads the charges of the pixels in combination). The image reading system of the gate line driver 71 may be switched between the sequential readout system and the binning readout system.

The image reading system may be switched between the sequential scanning system and an interlaced scanning system (interlaced scanning system) that divides the gate lines G into odd-numbered lines and even-numbered lines and, in each image readout operation, outputs on-signals to the odd-numbered gate lines G or the even-numbered gate lines G and reads the charges accumulated at the pixel portions of each line alternatingly.

The signal processing section 73 and the gate line driver 71 are connected to a cassette control section 69, and the gate line driver 71 and signal processing section 73 are controlled by the cassette control section 69. The cassette control section 69 is structured by a microcomputer including a CPU, a ROM, a RAM, an HDD, a flash memory and the like.

The arrangement of the pixels of the radiation detector 26 is not limited to a matrix array arranged in rows and columns. For example, another arrangement such as a staggered array or the like may be employed. Furthermore, as the shape of the pixels, pixels with a rectangular shape may be employed, and pixels with a hexagonal shape such as a honeycomb pattern or the like may be employed.

Figure 5:
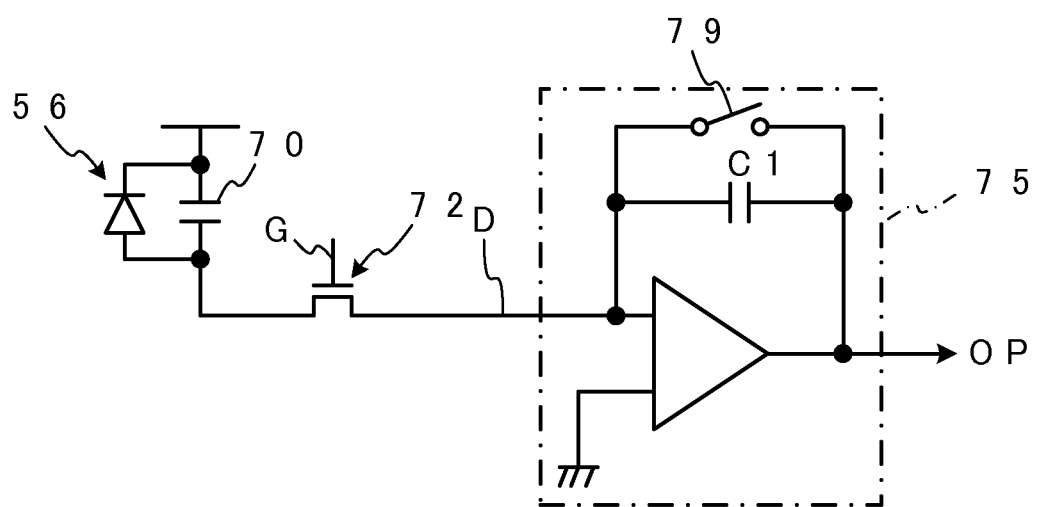
FIG. 5 is a diagram showing an equivalent circuit concerning a single-pixel portion of the radiation detector in accordance with the exemplary embodiment.

FIG. 4 is a block diagram showing schematic structure of the signal processing section 73 of the radiation detector 26 according to the exemplary embodiment. FIG. 5 is a diagram showing an equivalent circuit concerning a single-pixel portion of the radiation detector 26 according to the exemplary embodiment.

As shown in FIG. 4, the charges that have been photo-electrically converted by the scintillator 56 are read out by the thin film transistors 72 being turned on and are outputted to the signal processing section 73.

As shown in FIG. 4, the signal processing section 73 is equipped with charge amplifiers 75, sample-and-hold circuits 76, a multiplexer 77, an analog-to-digital (A/D) converter 78 and a bias current control section 81.

The charges read out by the thin film transistors 72 are integrated and amplified by a pre-specified amplification factor by the charge amplifiers 75, retained by the sample-and-hold circuits, and outputted to the A/D converter 78 via the multiplexer 77. The analog signals are converted to digital signals by the A/D converter 78, enabling image processing.

The pre-specified amplification factor mentioned above is determined on the basis of, for example, a frame rate, operation procedure, imaging subject area and the like, which are registered via a control menu, which is described below, displayed at the display 80. For example, in a case in which the frame rate is higher, the amplification factor is higher.

More specifically, as shown in FIG. 5, the source of each thin film transistor 72 is connected to one of the data lines D, and the data line D is connected to one of the charge amplifiers 75. The drain of the thin film transistor 72 is connected to the capacitor 70, and the gate of the thin film transistor 72 is connected to one of the gate lines G. The charge amplifiers 75 may be provided in correspondence with respective pixels (the thin film transistors 72), may be provided one for each column (each data line D), may be provided one for each of pre-specified groups (for example, groups of 3×3 pixels or the like), and may be provided one for each of pre-specified column groups (for example, a plural number of the data lines D).

The charge signals transmitted through an individual data line D are integrated by the charge amplifier 75 and retained at the sample-and-hold circuit 76. The charge amplifier 75 is provided with a reset switch 79. While the reset switch 79 is turned off, charges are read out and charge signals are retained at the sample-and-hold circuit 76. When a readout of charges has ended, the reset switch 79 is turned on, the charges remaining at an integration capacitor C1 of the charge amplifier 75 are discharged, and the charge amplifier 75 is reset. Resetting by the reset switch 79 corresponds to a resetter of the present invention.

The charge signals retained at the sample-and-hold circuits 76 are converted to analog voltages, sequentially (serially) inputted to the multiplexer 77, and converted to digital image information by the A/D converter 78.

The bias current control section 81 controls bias currents supplied to the charge amplifiers 75. In the present exemplary embodiment, control is performed such that, in accordance with pre-specified conditions, a bias current that is supplied to the charge amplifiers 75 when a reset is being implemented by the reset switch is altered. More specifically, in a case of video imaging, a shortening of a reset duration of the charge amplifiers 75 is enabled by the bias current being increased relative to a case of still imaging, and the cassette control section 69 controls the reset switches 79 such that the reset duration of the charge amplifiers 75 is shortened in accordance with the increase in the bias current. The bias current may be increased only at periods of resetting the charge amplifiers 75, but may also be increased during the video imaging. That is, it is sufficient that the bias current may be altered in at least some periods of resetting.

The pre-specified conditions mentioned above may be, for example, an imaging subject area, a radiation amount and the like just before imaging, and a frame rate, operation procedure, imaging subject area and the like that are recorded in a control menu just after imaging. For example, in a case of a still image examination with a large radiation amount just before imaging, the bias current supplied to the charge amplifiers 75 is increased. On the other hand, in a case in which a high frame rate is registered in a control menu just after imaging, the bias supplied to the charge amplifiers 75 may be reduced.

These thin film transistors 72 are controlled to turn on and off and the reset switches 79 of the charge amplifiers 75 are controlled to turn on and off by the cassette control section 69.

Figure 6:
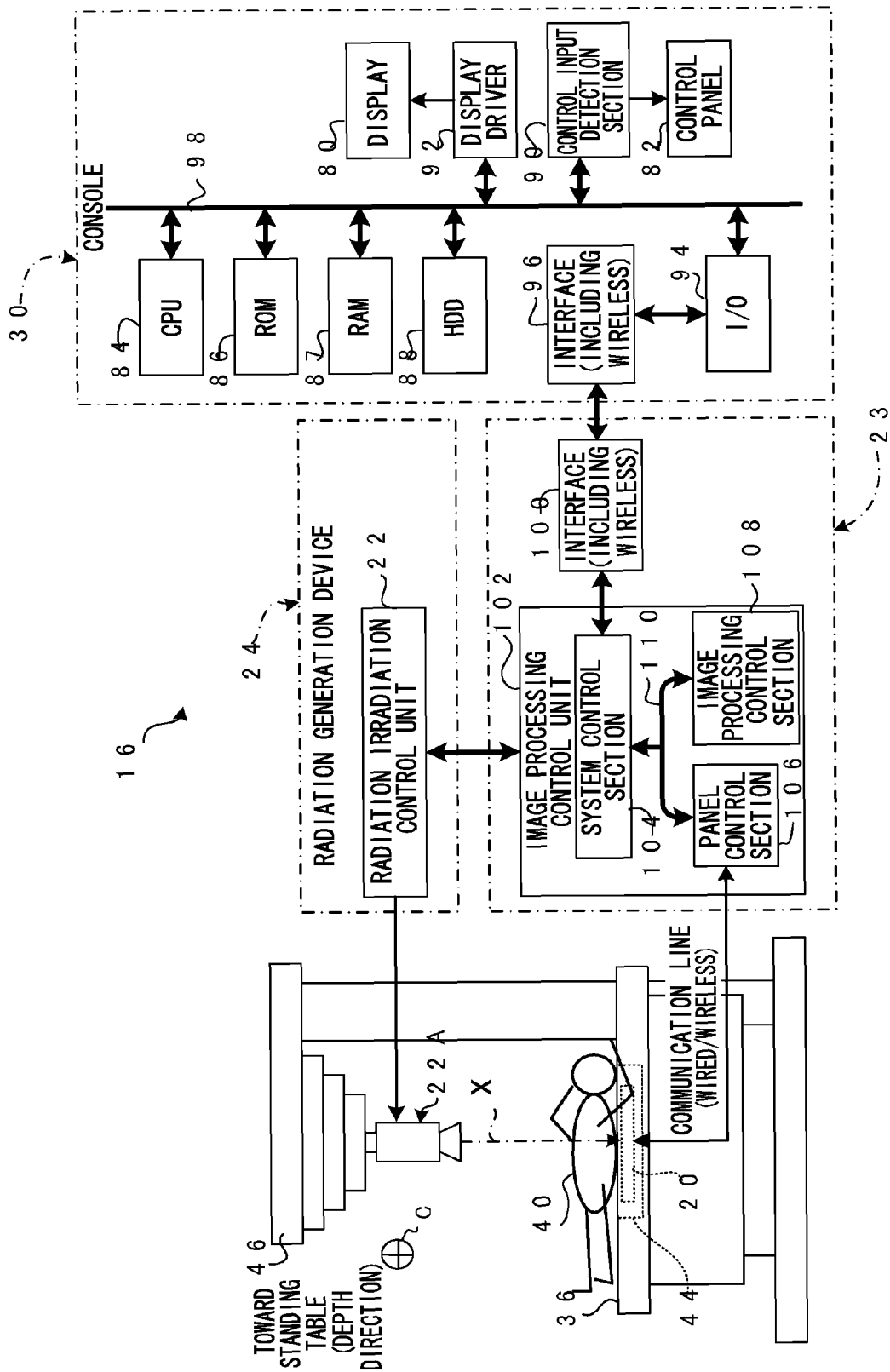
FIG. 6 is a control block diagram of an imaging system in accordance with the exemplary embodiment of the present invention.

FIG. 6 is a control block diagram of the imaging system 16 according to the present exemplary embodiment.

The console 30 is constituted as a server computer, and is equipped with a display 80, which displays control menus, imaged radiation images and the like, and a control panel 82, which is structured to include plural buttons and at which various kinds of information and control instructions can be inputted.

The console 30 according to the present exemplary embodiment is equipped with: a CPU 84 that administers operations of the device as a whole; a ROM 86 at which various programs, including a control program, and suchlike are stored in advance; a RAM 87 that temporarily stores various kinds of data; the HDD 88, which stores and retains various kinds of data; a display driver 92 that controls displays of various kinds of information at the display 80; and a control input detection section 90 that detects control states of the control panel 82.

The console 30 is further equipped with an interface (for example, a wireless communication section) 96 and an input/output (I/O) 94. The wireless communication section 96, by wireless communication, exchanges various kinds of information such as below-described exposure conditions and the like with an image processing device 23 and the radiation generation device 24 and exchanges various kinds of information such as image data and the like with the electronic cassette 20.

The CPU 84, ROM 86, RAM 87, HDD 88, display driver 92, control input detection section 90, I/O 94 and wireless communication section 96 are connected to one another by buses 98, such as a system bus and a control bus. Thus, the CPU 84 may access the ROM 86, RAM 87 and HDD 88, control displays of various kinds of information at the display 80 via the display driver 92 and, via the wireless communication section 96, control transmission and reception of various kinds of information to and from the radiation generation device 24 and the electronic cassette 20. The CPU 84 may also acquire states of control by users from the control panel 82 via the control input detection section 90.

The image processing device 23 is equipped with an interface (for example, a wireless communication section) 100 and an image processing control unit 102. The interface 100 exchanges various kinds of information such as irradiation conditions and the like with the console 30. The image processing control unit 102 controls the electronic cassette 20 and the radiation generation device 24 in accordance with the irradiation conditions. The radiation generation device 24 is equipped with the radiation irradiation control unit 22, which controls irradiations of radiation from the radiation irradiation source 22A.

The image processing control unit 102 is equipped with a system control section 104, a panel control section 106 and an image processing control section 108, which exchange information with one another through a bus 110. Information from the electronic cassette 20 is received at the panel control section 106 wirelessly or by wire, and image processing is conducted at the image processing control section 108. The reception of information from the electronic cassette 20 may, for example, be set to wireless communication in a case of video imaging, in order to assure communication rates, and be set to wireless communication in a case of still imaging.

The system control section 104 receives information such as a tube voltage, a tube current and the like in irradiation conditions from the console 30, and controls an irradiation of the radiation X from the radiation irradiation source 22A of the radiation irradiation control unit 22 on the basis of the received irradiation conditions.

Figure 7:
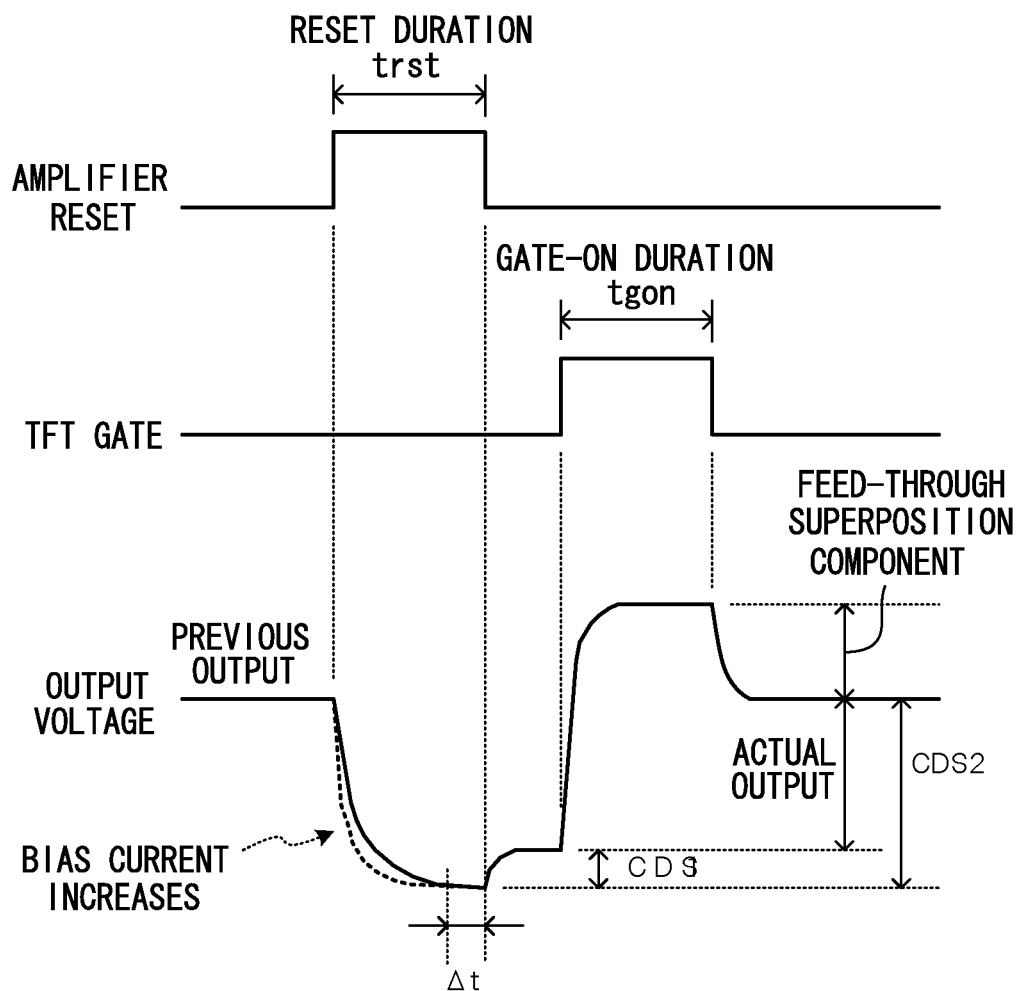
FIG. 7 is a diagram showing output waveforms when charges are read out from a charge amplifier.

Now, for the radiation detector 26 structured as described above, photoelectric conversion by the scintillator 56 and reading out of charges accumulated at the capacitors 70 is described. FIG. 7 is a diagram showing output waveforms when charges are read out from one of the charge amplifiers 75.

In the radiation detector 26, the charges accumulated at each capacitor 70 are read out by the thin film transistor 72 being turned on and off. Before a readout of charges, the operation to reset the charge amplifier 75 is performed in order to reset charges remaining at the integration capacitor C1 of the charge amplifier 75 from a previous readout.

The reset operation of the charge amplifier 75 is implemented by the reset switch 79 being turned on and off by the cassette control section 69. When the reset switch 79 is turned on by the cassette control section 69, as shown by the output voltage in FIG. 7, the output OP of the charge amplifier 75 is reset by charges being discharged during the reset duration test. Here, the charges are discharged with a time constant that depends on a response characteristic of the charge amplifier 75, and the discharge of charges reaches a saturated condition in some cases. Hence, when the reset switch 79 is turned off, a charge CDS1 is superimposed by the turning-off of the reset switch 79.

Then the gate of the thin film transistor 72 (the TFT gate) is turned on and charges are read out. The gate is turned off after the passage of a gate-on time tgon, and the readout of charges finishes. Feed-through noise is superimposed by the gate being turned on and off. However, a feed-through superimposition component is cancelled out by the integration by the charge amplifier 75, and a charge CDS2 is obtained. The difference between the charge CDS2 and the charge CDS1 is the actual output, and the actual output is what is calculated by the sample-and-hold circuit.

The charge CDS1 is not constant but random, and CDS1 is larger if the reset duration is short and charges are not completely discharged. However, because all values are shifted upward by the charge CDS1, in conditions such as a condition of imaging with small charges, there is no real problem.

Now, when the charge amplifier 75 is being reset, the charges are discharged with a time constant as mentioned above. However, the time constant characteristic may be altered and the discharge duration of the charges may be quickened, as shown by the broken line in FIG. 7, by increasing the bias current. In the example in FIG. 7, the discharge duration of the charges may be quickened by an amount of time $\Delta t$.

In the present exemplary embodiment, as described above, in a case of video imaging, the bias current control section 81 performs control so as to increase the bias current relative to a time of still imaging. In addition, the cassette control section 69 controls the reset switches 79 of the charge amplifiers 75 so as to shorten the reset duration. As a result, an imaging duration is shortened.

Figure 8A:
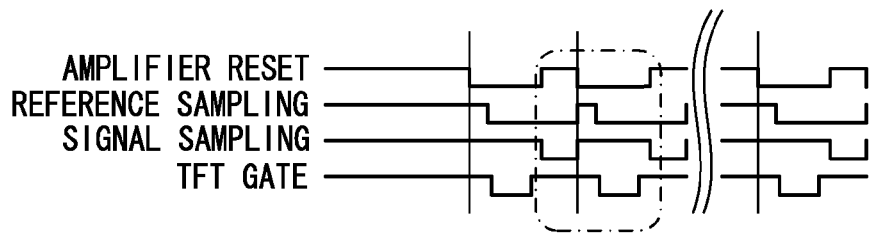
FIG. 8A is a chart showing, in a data readout period, amplifier resets by a reset switch, reference sampling at a sample-and-hold circuit, signal sampling at the sample-and-hold circuit, and on- and off-timings of the gate of a thin film transistor.
Figure 8B:
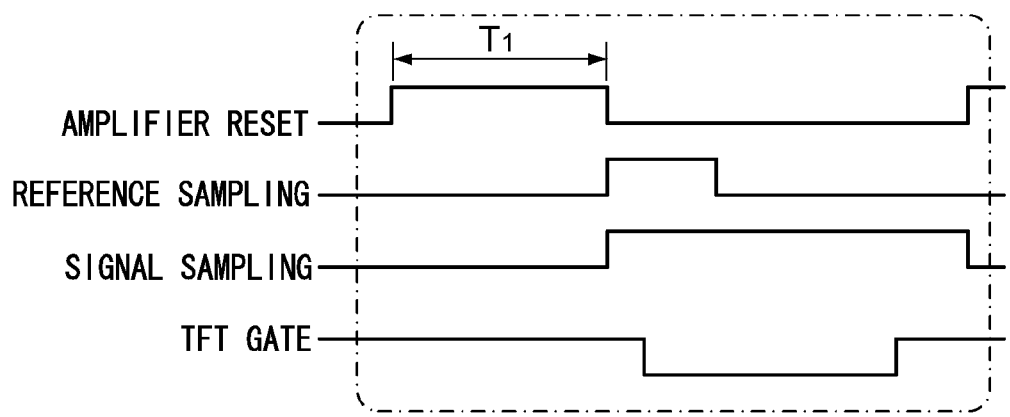
FIG. 8B is a magnified diagram of a data readout period, corresponding to one line in FIG. 8A.

FIG. 8A is a chart showing, in a data readout period, amplifier resets by one of the reset switches 79, reference sampling at the sample-and-hold circuit 76, signal sampling at the sample-and-hold circuit 76, and on- and off-timings of the gate of the thin film transistor 72. FIG. 8B is a magnified diagram of a data readout period corresponding to one line, and FIG. 8C is a diagram in which an amplifier reset duration is shortened.

Figure 8C:
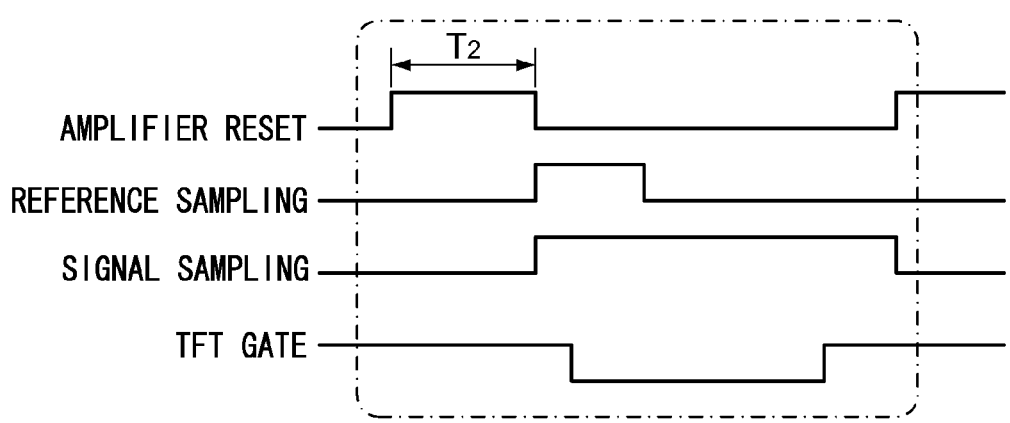
FIG. 8C is a diagram in which an amplifier reset duration of FIG. 8B is shortened.

In the present exemplary embodiment, if an amplifier reset duration for still imaging is a pre-specified standard duration, shown as T1 in FIG. 8B, in the case of video imaging, as shown in FIG. 8C, the on-duration of the reset switch 79 may be shortened to T2 (<T1) because the bias current is increased, and the amplifier reset duration may be shortened. Consequently, the readout duration is shortened, leading to a shortening of the imaging duration. An amount of shortening of the amplifier reset duration is determined in advance by experiment or the like. However, because a possible amount of shortening of the reset duration is dictated by an amount of increase in the bias current, the amount of increase in the bias current is determined first, and the amount of shortening of the reset current is determined in accordance with the amount of increase in the bias current. When the amount of increase in the bias current is large, a great shortening of the reset duration can be expected, but power consumption increases. When the amount of increase in the bias current is small, the amount of shortening of the reset duration is small and the effect of shortening the imaging duration is small. Therefore, the amount of increase may be determined in accordance with which of power consumption and imaging duration takes priority.

Next, operations of the present exemplary embodiment are described in accordance with the flowcharts in FIG. 9 to FIG. 12.

Figure 9:
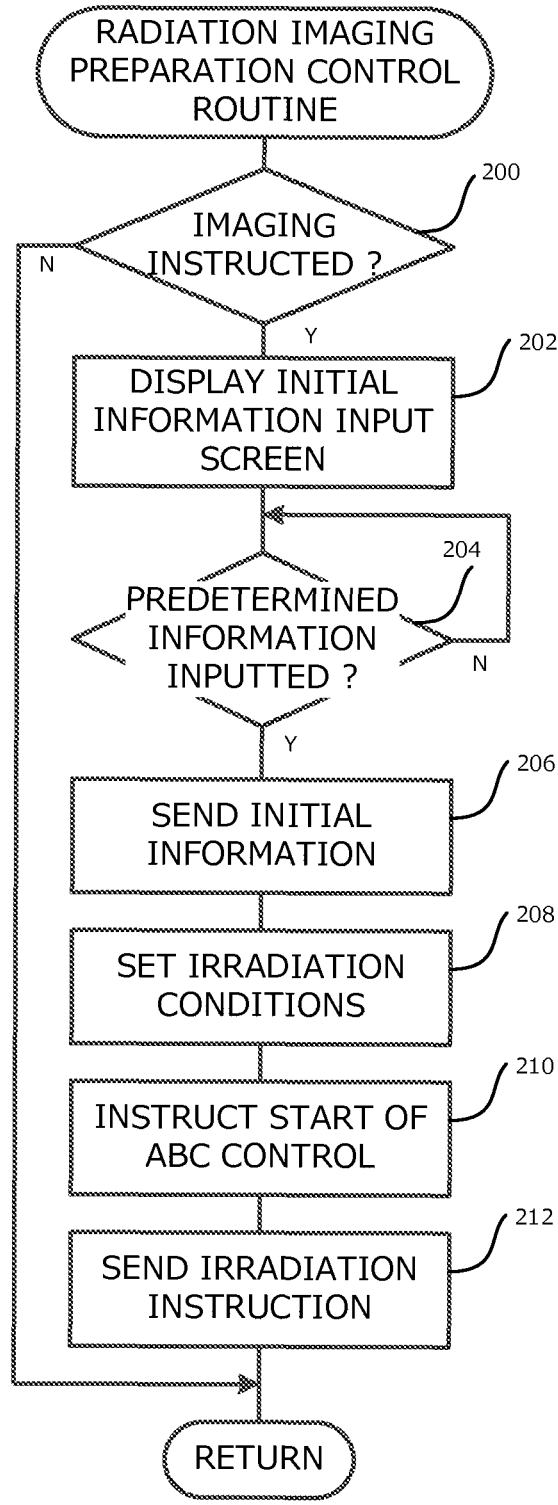
FIG. 9 is a flowchart showing a radiographic imaging preparation control routine in accordance with the exemplary embodiment of the present invention.

FIG. 9 is a flowchart showing a radiographic imaging preparation control routine.

In step 200, a determination is made as to whether an imaging instruction has been given. If the result of the determination is negative, the routine ends, and if the result is affirmative, the routine proceeds to step 202.

In step 202, an initial information input screen is displayed at the display 80, and the routine proceeds to step 204. That is, the display driver 92 is controlled such that a pre-specified initial information input screen is displayed by the display 80.

In step 204, a determination is made as to whether predetermined information has been inputted. The routine stands by until the result of the determination is affirmative, and then proceeds to step 206. The initial information input screen displays messages prompting the input of, for example, the name of an imaging subject of whom radiation images are to be captured thereafter, an imaging subject region, a posture during imaging, and irradiation conditions of the radiation X during the imaging (in the present exemplary embodiment, the tube voltage and tube current when the radiation X is being irradiated), and displays input regions for this information.

When the initial information input screen is displayed at the display 80, an imaging operator inputs at the respectively corresponding input fields, via the control panel 82, the name of the subject who is the object of imaging, the imaging target portion, the posture at the time of imaging, and the exposure conditions.

The imaging operator enters the radiography imaging room 32 together with the imaging subject. As an example, in a case of a reclining position, the electronic cassette 20 is retained at the corresponding retention portion 44 of the reclining table 36, and the radiation irradiation source 22A is positioned at a corresponding position, after which the imaging subject is placed (positioned) at a predetermined imaging location. In a case of capturing a radiation image in a state in which the electronic cassette 20 is not retained at a retention portion, such as when the imaging target portion is an arm area or a leg area, the imaging operator positions the imaging subject, the electronic cassette 20 and the radiation irradiation source 22A into a state in which the imaging target portion can be imaged.

Then, the imaging operator leaves the radiography imaging room 32 and, for example, clicks a "Complete" button displayed at a lower end vicinity of the initial information input screen via the control panel 82. When the Complete button is clicked by the imaging operator, the result of the determination in step 204 is affirmative and the routine proceeds to step 206. In the flowchart of FIG. 9, step 204 forms an endless loop. However, the routine may be forced to end by operation of a cancel button provided on the control panel 82.

In step 206, the information inputted into the initial information input screen (hereinafter referred to as initial information) is sent to the electronic cassette 20 via the wireless communication section 96. Then, the routine proceeds to step 208, and the exposure conditions included in the initial information are set by transmission of the exposure conditions to the radiation generation device 26 via the wireless communication section 96. Accordingly, the image processing control unit 102 of the radiation generation device 24 prepares for exposure with the received exposure conditions.

Then, in step 210, the start of ABC control is instructed. The routine proceeds to step 212, instruction information instructing the start of the irradiation of radiation is transmitted to the radiation generation device 24 via the wireless communication section 96, and the routine ends.

Figure 10:
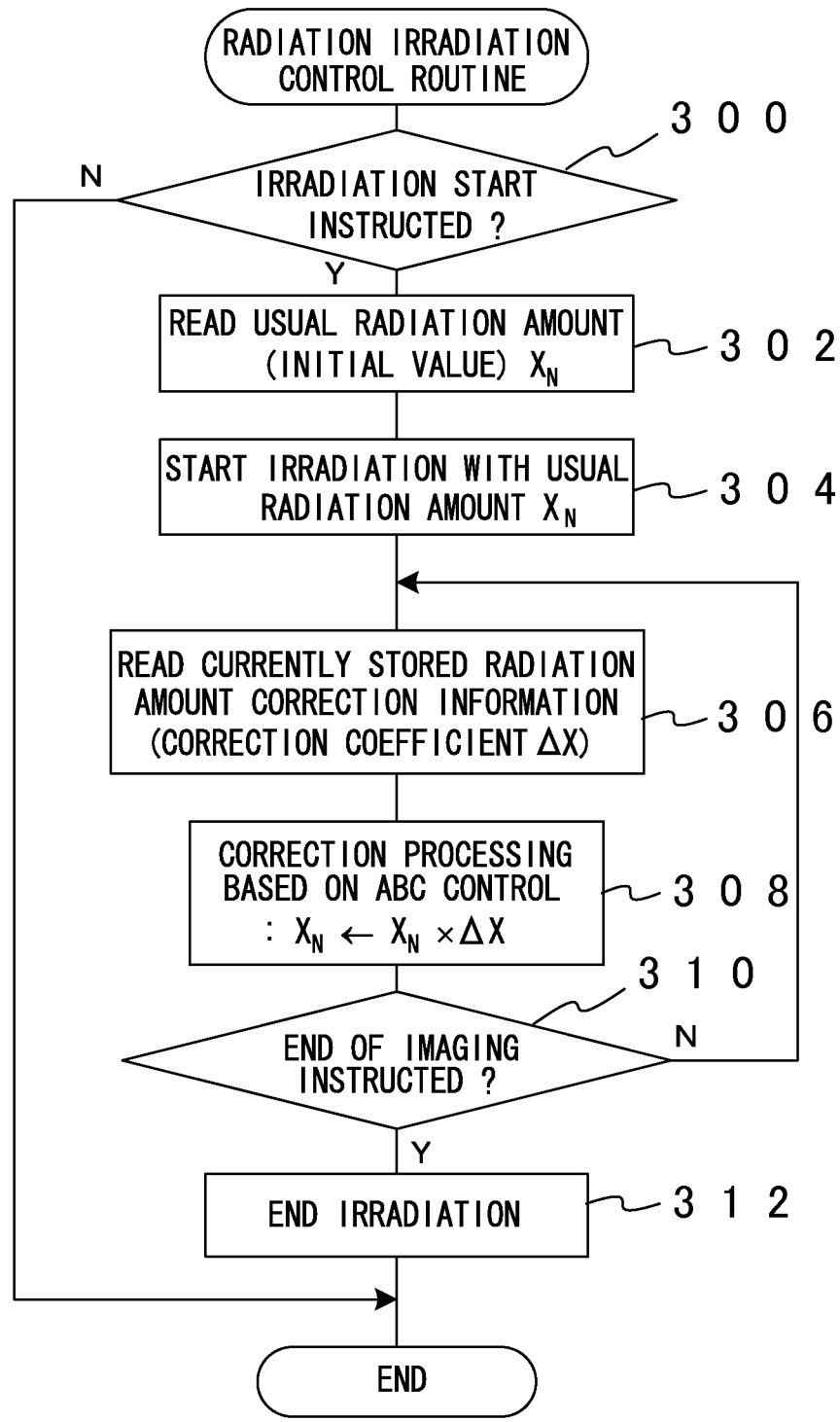
FIG. 10 is a flowchart showing a radiographic imaging control routine in accordance with the exemplary embodiment of the present invention.

Now, the flow of radiation irradiation control is described in accordance with the flowchart of FIG. 10. FIG. 10 is a flowchart showing a radiation irradiation control routine.

In step 300, a determination is made as to whether the start of the radiation has been instructed. If the result of the determination is negative, the routine ends, and if the result is affirmative, the routine proceeds to step 302.

In step 302, a usual radiation amount (an initial value) $X_N$ is read in, and the routine proceeds to step 304.

In step 304, irradiation is commenced with the usual radiation amount that has been read in, and the routine proceeds to step 306. That is, an irradiation from the radiation irradiation source 22A is commenced by applying a tube voltage and tube current in accordance with an irradiation maximum received from the console 30 to the radiation generation device 24. The radiation X emitted from the radiation irradiation source 22A reaches the electronic cassette 20 after passing through the imaging subject.

In step 306, currently stored radiation amount correction information is read in, and the routine proceeds to step 308. This radiation amount correction information is generated by the ABC control, and is stored as a correction coefficient $\Delta X$.

Then, in step 308, correction processing is executed on the basis of the ABC control, and the routine proceeds to step 310. That is, on the basis of gradation signals (QL values) obtained from the electronic cassette 20, an average value of the QL values in an image of a region of interest is calculated, the average of the QL values is compared with a pre-specified threshold value, and feedback control is applied to the radiation amounts such that the average of the QL values converges with the threshold value.

In step 310, a determination is made as to whether the end of imaging has been instructed. If the result of the determination is affirmative, the routine proceeds to step 312, and if the result is negative, the routine returns to step 306 and repeats the processing described above.

In step 312, the irradiation is ended and the radiographic imaging control ends.

Figure 11:
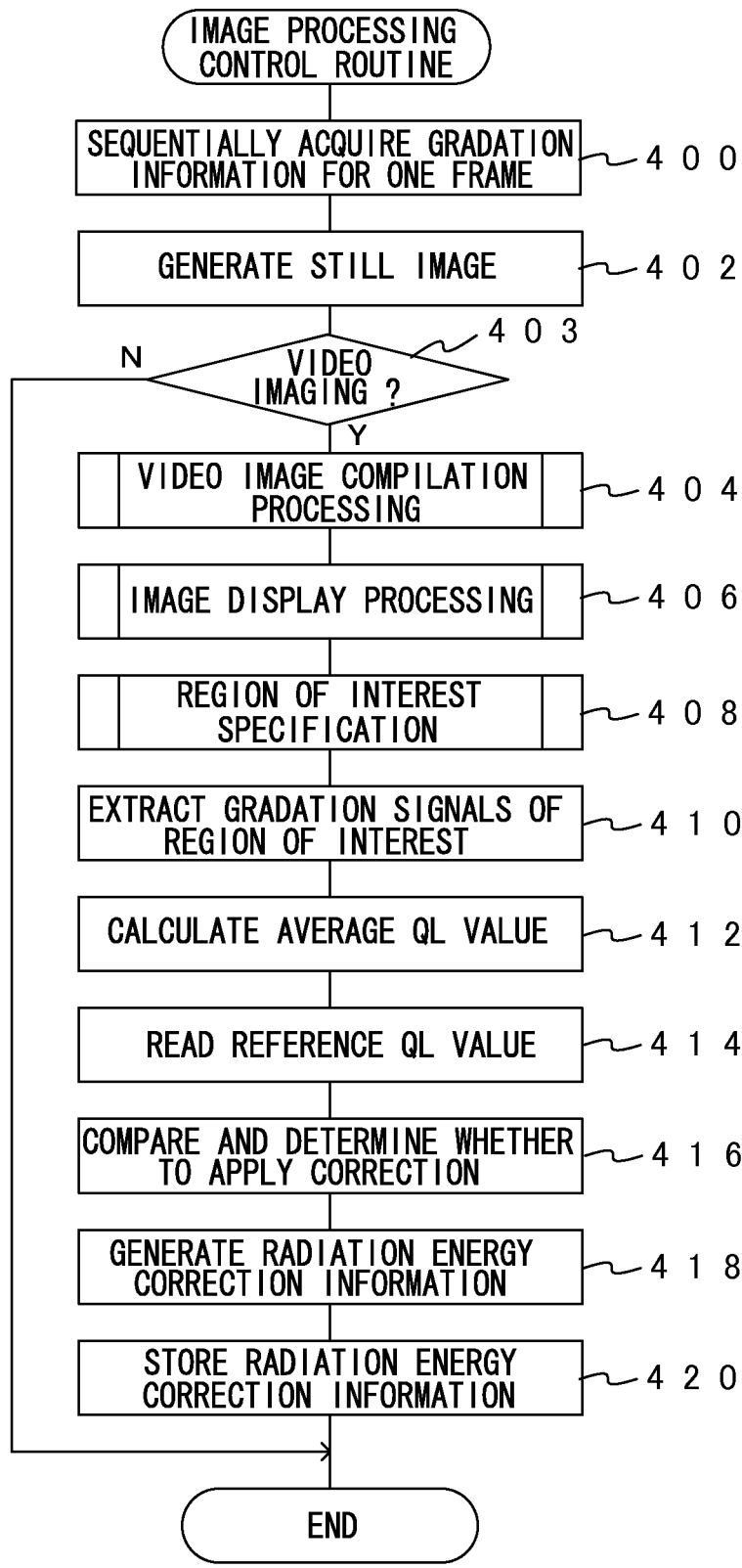
FIG. 11 is a flowchart showing an image processing control routine in accordance with the exemplary embodiment of the present invention.

Now, the flow of radiation processing control is described in accordance with the flowchart of FIG. 11. FIG. 11 is a flowchart showing an image processing control routine.

When the radiographic imaging control is carried out as described above, in step 400, gradation information corresponding to a single frame is sequentially acquired, and the routine proceeds to step 402. That is, gradation signals generated by the TFT substrate 74 of the electronic cassette 20 are sequentially acquired by the image processing control unit 102 under the control of the panel control section 106. Before the gradation signals are acquired by the image processing control unit 102, the gradation signals are sequentially acquired by the cassette control section 69 in accordance with gradation signal acquisition processing, which is described below, and the gradation signals acquired by the cassette control section 69 are sequentially sent to the image processing control unit 102 under the control of the panel control section 106.

In step 402, a still image is generated, and the routine proceeds to step 403. That is, the still image is generated when the gradation signals corresponding to the single frame have been acquired.

In step 403, a determination is made as to whether video imaging is being performed. If the result of the determination is affirmative, the routine proceeds to step 404, and if the result is negative, the image processing control simply ends.

In step 404, video image compilation processing is carried out, and the routine proceeds to step 406. In the video image compilation processing, still images corresponding to the single frames generated in step 402 are combined to compile a video image.

In step 406, image display processing is carried out, and the routine proceeds to step 408. In the image display processing, the video image created by the video image compilation processing is sent to the display driver 92, and hence is displayed at the display 80 by the display driver 92.

In step 408, region of interest specification is carried out, and the routine proceeds to step 410. In the region of interest specification, a region of interest is specified by, for example, pattern-matching or the detection of a region with a large amount of movement, or the region of interest may be specified by operations by a user.

In step 410, the gradation signals of the specified region of interest are extracted, and the routine proceeds to step 412.

In step 412, the average QL value of the gradation signals of the region of interest is calculated, and the routine proceeds to step 414. In step 414, a pre-stored reference QL value is read in, and the routine proceeds to step 416.

In step 416, the calculated average QL value is compared with the reference QL value that has been read in, a determination is made as to whether to apply correction, and the routine proceeds to step 418. The determination of whether to apply correction may be, for example, an on/off determination such that correction by a pre-specified amount is applied if a difference found by the comparison is at least a predetermined value but correction is not applied if the difference is less than the predetermined value. The determination may also be the solution of a computation based on a pre-specified computational formula based on the difference (for example, a computation formula based on PID control or the like).

In step 418, on the basis of the comparison and correction applicability determination results of step 416, the radiation amount correction information $\Delta X$ is generated, and the routine proceeds to step 420.

In step 420, the generated correction information $\Delta X$ is stored, and the image processing control ends.

Figure 12:
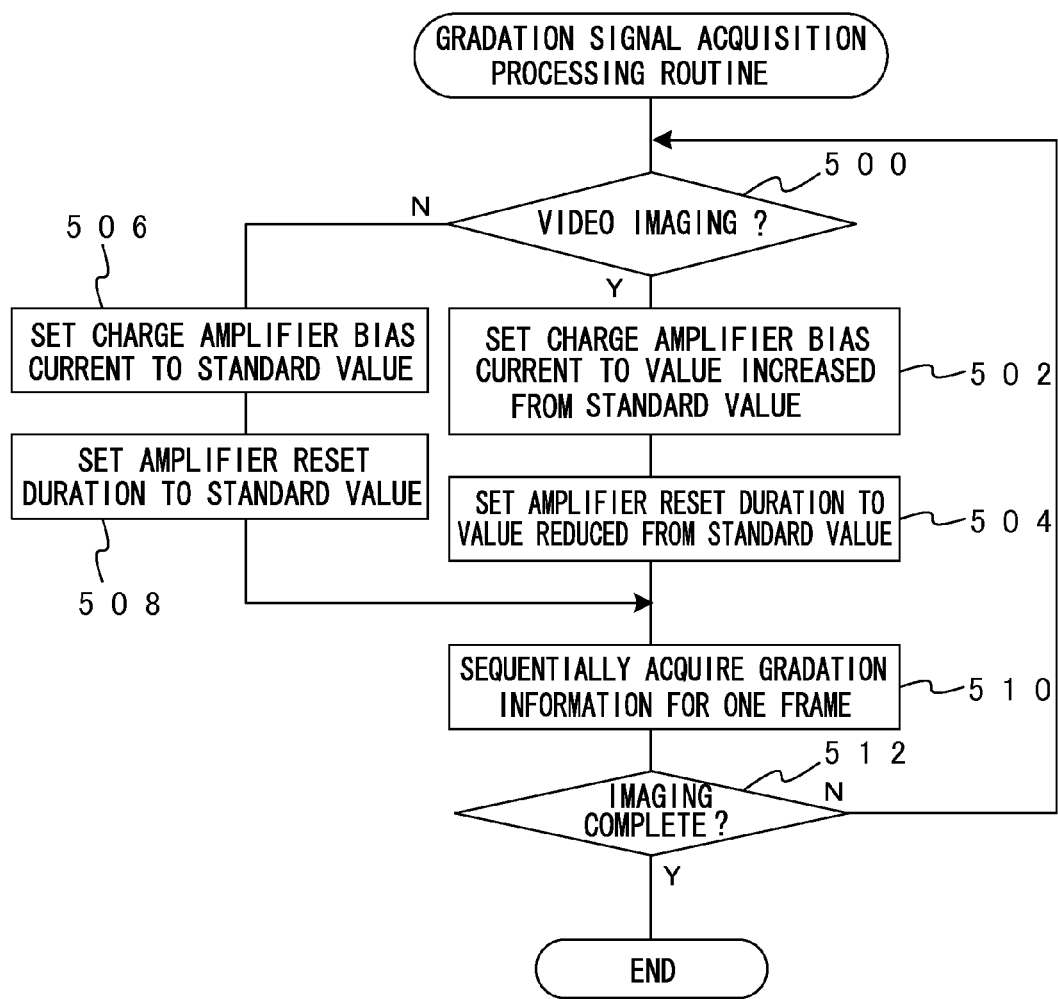
FIG. 12 is a flowchart showing a gradation signal acquisition processing routine in accordance with the exemplary embodiment of the present invention.

Now, the flow of gradation signal acquisition processing that is carried out at the cassette control section 69 when the above-mentioned gradation signals are being sequentially acquired is described in accordance with the flowchart of FIG. 12. FIG. 12 is a flowchart showing a gradation signal acquisition processing routine.

When the gradation signals are to be acquired, first, a determination is made in step 500 as to whether video imaging is being performed. This determination determines, for example, whether or not video imaging has been instructed by the control panel 82. If the result of the determination is affirmative, the cassette control section 69 proceeds to step 502, and if the result is negative, the cassette control section 69 proceeds to step 506. The transmission of information from the electronic cassette 20 to the panel control section 106 may be by wired communication in a case of video imaging and by wireless communication in a case of still imaging, and the determination may be a determination as to whether wired communication is being used.

In step 502, the bias current of the charge amplifiers 75 is set by the bias current control section 81 to a value that is increased from a pre-specified standard value, and the cassette control section 69 proceeds to step 504.

In step 504, the amplifier reset duration of the charge amplifiers 75 is set to a value that is shortened from a pre-specified standard value, and the cassette control section 69 proceeds to step 510. The amount of shortening of the amplifier reset duration is specified beforehand in accordance with, for example, experimentation or the like.

Alternatively, in step 506, the bias current of the charge amplifiers 75 is set by the bias current control section 81 to the pre-specified standard value, and the cassette control section 69 proceeds to step 508.

In step 508, the amplifier reset duration of the charge amplifiers 75 is set to the pre-specified standard value, and the cassette control section 69 proceeds to step 510.

In step 510, gradation signals corresponding to one signal frame are sequentially acquired, and the routine proceeds to step 512. That is, when a still image is being imaged, as shown in FIG. 8B, the amplifier reset duration is at the standard value and when a video image is being imaged, as shown in FIG. 8C, the amplifier reset duration for which the reset switches 79 are turned on for each line is made shorter than the standard duration, and the gradation signals are sequentially read out. Therefore, in a case of video imaging, the imaging duration may be shortened and the burden on the imaging subject may be moderated.

In step 512, a determination is made as to whether imaging is complete. If the result of the determination is negative, the cassette control section 69 returns to step 500 and the processing described above is repeated, and if the result is affirmative, the sequence of processing ends.

Thus, in the present exemplary embodiment, utilizing the fact that the reset duration may be shortened in a case of video imaging by increasing the bias current of the charge amplifiers 75 relative to still imaging, the charges accumulated at the capacitors 70 when imaging a video image may be read out with the bias current of the charge amplifiers 75 increased and the reset duration shortened, and thus an imaging duration may be shortened by an amount corresponding to the shortening of the amplifier reset duration.

Hence, an amount of radiation irradiated at the imaging subject may be reduced by the imaging duration being shortened, and the burden on the imaging subject may be moderated.

In the exemplary embodiment described above, the bias current of the charge amplifiers 75 is increased in a case of video imaging compared to still imaging and the reset duration is shortened. However, conditions in which the bias current is increased are not limited thus, and the bias current may be increased and the reset duration shortened in accordance with other conditions. For example, in a case of still imaging in which the reading duration should be shortened even if the power consumption increases (a case in which shortening the imaging duration takes precedence over power consumption), the bias current may be increased and the reset duration shortened.

In the exemplary embodiment described above, an increase in the bias current of the charge amplifiers 75 and a shortening of the reset duration are applied together, and the imaging duration is shortened. However, an increase of the bias current alone may be applied. For example, because remaining charges may be more reliably discharged by increasing the bias current, instead of shortening the reset duration and shortening the imaging duration, the reset duration may be kept the same and a more accurate image may be obtained.

The processing of the flowcharts in the exemplary embodiment described above may be memorized as programs in respective storage media and these may be distributed.

Variant Example 1

The nonvolatile computer readable storage medium stores a radiographic imaging control program that causes a computer to execute a process including: (a) with a resetter of an amplifier, resetting charges remaining at an integration capacitor before imaging, the amplifier being provided in correspondence with a respective pixel of a radiation detector in which a plurality of the pixels are arrayed, each pixel including a sensor portion that generates charges in accordance with irradiated radiation and a switching element that is for reading out the charges generated at the sensor portion, and the amplifier being equipped with the resetter that resets the remaining charges and amplifying an electronic signal according to the charges read out by the switching element from the corresponding pixel by a pre-specified amplification factor; and (b) in accordance with a pre-specified condition, controlling so as to alter a bias current supplied to the amplifier in at least some periods of resetting by the resetter in (a).

Variant Example 2

In the computer readable storage medium recited in variant example 1, (b) further includes controlling so as to alter a reset duration by the resetter in accordance with the alteration of the bias current.

Variant Example 3

In the computer readable storage medium recited in variant example 1, (b) includes controlling so as to increase the bias current.

Variant Example 4

In the computer readable storage medium recited in variant example 3, when a video image is being imaged, (b) includes controlling so as to increase the bias current relative to when a still image is being imaged.

Variant Example 5

In the computer readable storage medium recited in variant example 3, when a video image is being imaged, (b) includes controlling so as to increase the bias current and shorten the reset duration relative to when a still image is being imaged.

Variant Example 6

In the computer readable storage medium recited in any of variant examples 1 to 5, (b) includes controlling so as to alter the bias current in accordance with a communication state of a communicator that implements wired communication when a video image is being imaged and implements wireless communication when a still image is being imaged.

An aspect of a radiographic imaging control device according to the present invention includes: a radiation detector in which a plurality of pixels are arrayed, each pixel including a sensor portion that generates charges in accordance with irradiated radiation and a switching element that is for reading out the charges generated at the sensor portion; an amplifier that is provided in correspondence with a respective pixel of the radiation detector, is equipped with a resetter that resets charges remaining at an integration capacitor, and amplifies an electronic signal according to the charges read out by the switching element from the corresponding pixel by a pre-specified amplification factor; and a controller that, in accordance with a pre-specified condition, controls so as to alter a bias current supplied to the amplifier in at least some periods of resetting by the resetter.

According to the radiographic imaging control device of the present invention, the plural pixels whose structures include sensor portions and switching elements are arrayed in the radiation detector, electric charges are generated in the sensor portions in accordance with irradiated radiation, and the charges are read out by the switching elements.

Each amplifier is provided in correspondence with a respective pixel/pixels of the radiation detector, is provided with the resetter that resets charges remaining in the integrating capacitor, and amplifies the electronic signals based on the charges read out from the corresponding pixel/pixels by the pre-specified amplification factor.

The controller performs control in accordance with pre-specified conditions so as to alter the bias current supplied to the amplifiers in at least some periods of resetting by the resetters. For example, the controller may shorten a duration in which charges are reset by the resetters, by controlling so as to increase the bias current supplied to the amplifiers in a case of video imaging and in a case in which imaging speed is prioritized over power consumption, or the like. Thus, the reset duration may be shortened. In consequence, an imaging duration may be shortened, amounts of radiation irradiated at an imaging subject may be reduced, and the burden on the imaging subject may be moderated.

The controller may further control so as to alter a reset duration by the resetter in accordance with the alteration of the bias current. The controller may control so as to increase the bias current. When a video image is being imaged, the controller may control so as to increase the bias current relative to when a still image is being imaged. When a video image is being imaged, the controller may control so as to increase the bias current and shorten the reset duration relative to when a still image is being imaged.

The radiographic imaging control device of the present invention may further include a communicator that implements wired communication when a video image is being imaged and implements wireless communication when a still image is being imaged, and the controller may control so as to alter the bias current in accordance with a communication state of the communicator.

The present invention may be configured as a radiographic imaging system that includes: a radiographic imaging control device according to any of the aspects described above; and a radiation irradiator that irradiates radiation at the radiation detector through an imaging subject.

A radiographic imaging device control method according to the present invention includes: (a) with a resetter of an amplifier, resetting charges remaining at an integration capacitor before imaging, the amplifier being provided in correspondence with a respective pixel of a radiation detector in which a plurality of the pixels are arrayed, each pixel including a sensor portion that generates charges in accordance with irradiated radiation and a switching element that is for reading out the charges generated at the sensor portion, and the amplifier being equipped with the resetter that resets the remaining charges and amplifying an electronic signal according to the charges read out by the switching element from the corresponding pixel by a pre-specified amplification factor; and (b) in accordance with a pre-specified condition, controlling so as to alter a bias current supplied to the amplifier in at least some periods of resetting by the resetter in (a).

According to the radiographic imaging device control method of the present invention, in (a), the generated charges in the sensor portions are reset before imaging by the resetters of the amplifiers that are provided in correspondence with the respective pixels of the radiation detector. Each amplifier is provided with the resetter that resets charges remaining in the integrating capacitor, and the amplifier amplifies the electronic signals based on the charges read out from the corresponding pixel by the pre-specified amplification factor.

In (b), control is performed in accordance with pre-specified conditions so as to alter the bias current supplied to the amplifiers in at least some periods of resetting by the resetters in (a). For example, in (b), the duration in which charges are reset by the resetters may be shortened by controlling so as to increase the bias current supplied to the amplifiers in a case of video imaging and in a case in which imaging speed is prioritized over power consumption, or the like. Thus, the reset duration may be shortened. In consequence, an imaging duration may be shortened, amounts of radiation irradiated at an imaging subject may be reduced, and the burden on the imaging subject may be moderated.

(b) may further include controlling so as to alter a reset duration by the resetter in accordance with the alteration of the bias current. (b) may include controlling so as to increase the bias current. When a video image is being imaged, (b) may include controlling so as to increase the bias current relative to when a still image is being imaged. When a video image is being imaged, (b) may include controlling so as to increase the bias current and shorten the reset duration relative to when a still image is being imaged. (b) may include controlling so as to alter the bias current in accordance with a communication state of a communicator that implements wired communication when a video image is being imaged and implements wireless communication when a still image is being imaged.

A radiographic imaging control program according to the present invention includes: (a) with a resetter of an amplifier, resetting charges remaining at an integration capacitor before imaging, the amplifier being provided in correspondence with a respective pixel of a radiation detector in which a plurality of the pixels are arrayed, each pixel including a sensor portion that generates charges in accordance with irradiated radiation and a switching element that is for reading out the charges generated at the sensor portion, and the amplifier being equipped with the resetter that resets the remaining charges and amplifying an electronic signal according to the charges read out by the switching element from the corresponding pixel by a pre-specified amplification factor; and (b) in accordance with a pre-specified condition, controlling so as to alter a bias current supplied to the amplifier in at least some periods of resetting by the resetter in (a).

According to the radiographic imaging control program of the present invention, in (a), the generated charges in the sensor portions are reset before imaging by the resetters of the amplifiers that are provided in correspondence with the respective pixels of the radiation detector. Each amplifier is provided with the resetter that resets charges remaining in the integrating capacitor, and the amplifier amplifies the electronic signals based on the charges read out from the corresponding pixel by the pre-specified amplification factor.

In (b), control is performed in accordance with pre-specified conditions so as to alter the bias current supplied to the amplifiers in at least some periods of resetting by the resetters in (a). For example, in (b), the duration in which charges are reset by the resetters may be shortened by controlling so as to increase the bias current supplied to the amplifiers in a case of video imaging and in a case in which imaging speed is prioritized over power consumption, or the like. Thus, the reset duration may be shortened. In consequence, an imaging duration may be shortened, amounts of radiation irradiated at an imaging subject may be reduced, and the burden on the imaging subject may be moderated.

(b) may further include controlling so as to alter a reset duration by the resetter in accordance with the alteration of the bias current. (b) may include controlling so as to increase the bias current. When a video image is being imaged, (b) may include controlling so as to increase the bias current relative to when a still image is being imaged. When a video image is being imaged, (b) may include controlling so as to increase the bias current and shorten the reset duration relative to when a still image is being imaged. (b) may include controlling so as to alter the bias current in accordance with a communication state of a communicator that implements wired communication when a video image is being imaged and implements wireless communication when a still image is being imaged.

In the present invention as described hereabove, the reset duration may be shortened by performing control in accordance with pre-specified conditions so as to alter the bias current supplied to the amplifiers when a reset is being carried out. Thus, excellent effects are provided in that imaging durations may be shortened and the burden on imaging subjects may be moderated.

The disclosures of Japanese Patent Application No. 2012-036717 are incorporated into the present specification by reference in their entirety.

All references, patent applications and technical specifications cited in the present specification are incorporated by reference into the present specification to the same extent as if the individual references, patent applications and technical specifications were specifically and individually recited as being incorporated by reference.

What is claimed is:

1. A radiographic imaging system control device comprising:
   a radiation detector in which a plurality of pixels are arrayed, each pixel including a sensor portion that generates charges in accordance with incident radiation and a switching element that is for reading out the charges generated at the sensor portion;
   an amplifier that is provided in correspondence with a respective pixel of the radiation detector, wherein said amplifier is equipped with a resetter that resets charges remaining at an integration capacitor, and amplifies an electronic signal according to the charges read out by the switching element from the corresponding pixel by a pre-specified amplification factor; and
   a controller with processing circuitry configured to, in accordance with a pre-specified condition, control the radiographic imaging system so as to alter a bias current supplied to the amplifier in at least some periods of resetting by the resetter, wherein the processing circuitry of the controller further controls so as to alter a reset duration by the resetter in accordance with the alteration of the bias current.

2. The radiographic imaging control device according to claim 1, wherein the controller controls so as to increase the bias current.

3. The radiographic imaging control device according to claim 1, wherein, in a case of imaging a video image, the controller controls so as to increase the bias current relative to a case of imaging a still image.

4. The radiographic imaging control device according to claim 1, wherein, in a case of imaging a video image, the controller controls so as to increase the bias current and shorten the reset duration relative to a case of imaging a still image.

5. The radiographic imaging control device according to claim 1, further comprising a communicator that implements wired communication when a video image is being imaged and implements wireless communication when a still image is being imaged,
wherein the controller controls so as to alter the bias current in accordance with a communication state of the communicator.

6. A radiographic imaging system comprising:
a radiographic imaging control device according to claim 1; and
a radiation source that emits radiation toward the radiation detector through an imaging subject.

7. A radiographic imaging device control method comprising:
(a) with a resetter of an amplifier, resetting charges remaining at an integration capacitor before imaging, the amplifier being provided in correspondence with a respective pixel of a radiation detector in which a plurality of the pixels are arrayed, each pixel including a sensor portion that generates charges in accordance with incident radiation and a switching element that is for reading out the charges generated at the sensor portion, and wherein the amplifier is equipped with the resetter that resets the remaining charges and amplifies an electronic signal according to the charges read out by the switching element from the corresponding pixel by a pre-specified amplification factor; and
(b) in accordance with a pre-specified condition, controlling the radiographic imaging device so as to alter a bias current supplied to the amplifier in at least some periods of resetting by the resetter in (a),
wherein the controller further controls so as to alter a reset duration by the resetter in accordance with the alteration of the bias current.

8. The radiographic imaging device control method according to claim 7, wherein (b) further includes controlling so as to alter a reset duration by the resetter in accordance with the alteration of the bias current.

9. The radiographic imaging device control method according to claim 7, wherein (b) includes controlling so as to increase the bias current.

10. The radiographic imaging device control method according to claim 7, wherein, in a case of imaging a video image, (b) includes controlling so as to increase the bias current relative to a case of imaging a still image.

11. The radiographic imaging device control method according to claim 7, wherein, in a case of imaging a video image, (b) includes controlling so as to increase the bias current and shorten the reset duration relative to a case of imaging a still image.

12. The radiographic imaging device control method according to claim 7, wherein (b) includes controlling so as to alter the bias current in accordance with a communication state of a communicator that implements wired communication when a video image is being imaged and implements wireless communication when a still image is being imaged.

13. A non-transitory recording medium storing a radiographic imaging system control program that causes a computer to execute a process comprising:
(a) with a resetter of an amplifier, resetting charges remaining at an integration capacitor before imaging, the amplifier being provided in correspondence with a respective pixel of a radiation detector in which a plurality of the pixels are arrayed, each pixel including a sensor portion that generates charges in accordance with incident radiation and a switching element that is for reading out the charges generated at the sensor portion, and wherein the amplifier is equipped with the resetter that resets the remaining charges and amplifies an electronic signal according to the charges read out by the switching element from the corresponding pixel by a pre-specified amplification factor; and
(b) in accordance with a pre-specified condition, controlling the radiographic imaging system so as to alter a bias current supplied to the amplifier in at least some periods of resetting by the resetter in (a),
wherein the controller further controls so as to alter a reset duration by the resetter in accordance with the alteration of the bias current.

14. The recording medium according to claim 13, wherein (b) further includes controlling so as to alter a reset duration by the resetter in accordance with the alteration of the bias current.

15. The recording medium according to claim 13, wherein (b) includes controlling so as to increase the bias current.

16. The recording medium according to claim 15, wherein, in a case of imaging a video image, (b) includes controlling so as to increase the bias current relative to in a case of imaging a still image.

17. The recording medium according to claim 15, wherein, in a case of imaging a video image, (b) includes controlling so as to increase the bias current and shorten the reset duration relative to a case of imaging a still image.

18. The recording medium according to any one of claim 13, wherein (b) includes controlling so as to alter the bias current in accordance with a communication state of a communicator that implements wired communication when a video image is being imaged and implements wireless communication when a still image is being imaged.

* * * * *